United States Patent [19]
Lerner et al.

[11] Patent Number: 6,010,225
[45] Date of Patent: Jan. 4, 2000

[54] FORWARD DUAL VIEWING DEVICE

[76] Inventors: Peter A. Lerner, 345 E. 73rd St. 3E, New York, N.Y. 10019; Perry J. Castellano, 6 N. Ross Dr., Yorktown Heights, N.Y. 10598

[21] Appl. No.: 08/938,071

[22] Filed: Sep. 26, 1997

[51] Int. Cl.[7] .................................................. G02B 7/182
[52] U.S. Cl. .................. 359/872; 359/850; 359/862; 359/865; 359/871; 359/879; 359/880; 359/882
[58] Field of Search ................................ 5/632; 224/616, 224/908; 359/850, 855, 856, 857, 862, 865, 871, 872, 873, 875, 879, 880, 882

[56] References Cited

U.S. PATENT DOCUMENTS

| | | | |
|---|---|---|---|
| 4,930,884 | 6/1990 | Tichenor et al. | 350/624 |
| 5,408,713 | 4/1995 | Stratton et al. | 5/632 |

OTHER PUBLICATIONS

The Retina Institute of Maryland, Macular Hole, Patient Information Literature (brochure); cover and pp. 1–10.

Face–Down, Oakworks is the Vitrectomy Support Solution (advertisement), Ophthalmic Surgery and Lasers, Jul. 1996.

V. R. Post Operative Device, (copy of product brochure), 2 pages, Palex Inventions, Inc., Great Barrinton, Mass.

*Primary Examiner*—Cassandra Spyrou
*Assistant Examiner*—Craig Curtis

[57] ABSTRACT

The present invention comprises viewing devices for use by those who must maintain a head down position, such as those who have undergone a surgical procedure for reattachment of the retina or repair of a macular hole, wherein a gas bubble is injected into the eye. The bubble, which is used to maintain the juxtaposition of the healing tissues, applies pressure upwards. If the surgical site is at the back of the eye, the postoperative patient needs to maintain a facedown position, for the bubble to maintain the retina against the back of the eye until the tear, detachment or hole is mended.

5 Claims, 11 Drawing Sheets

FIG. 10a
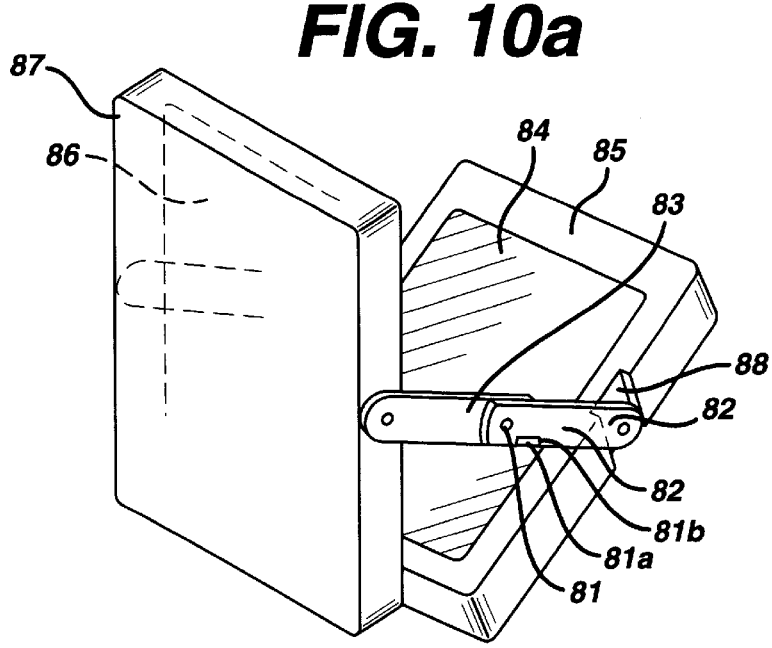
FIG. 10b
FIG. 10c
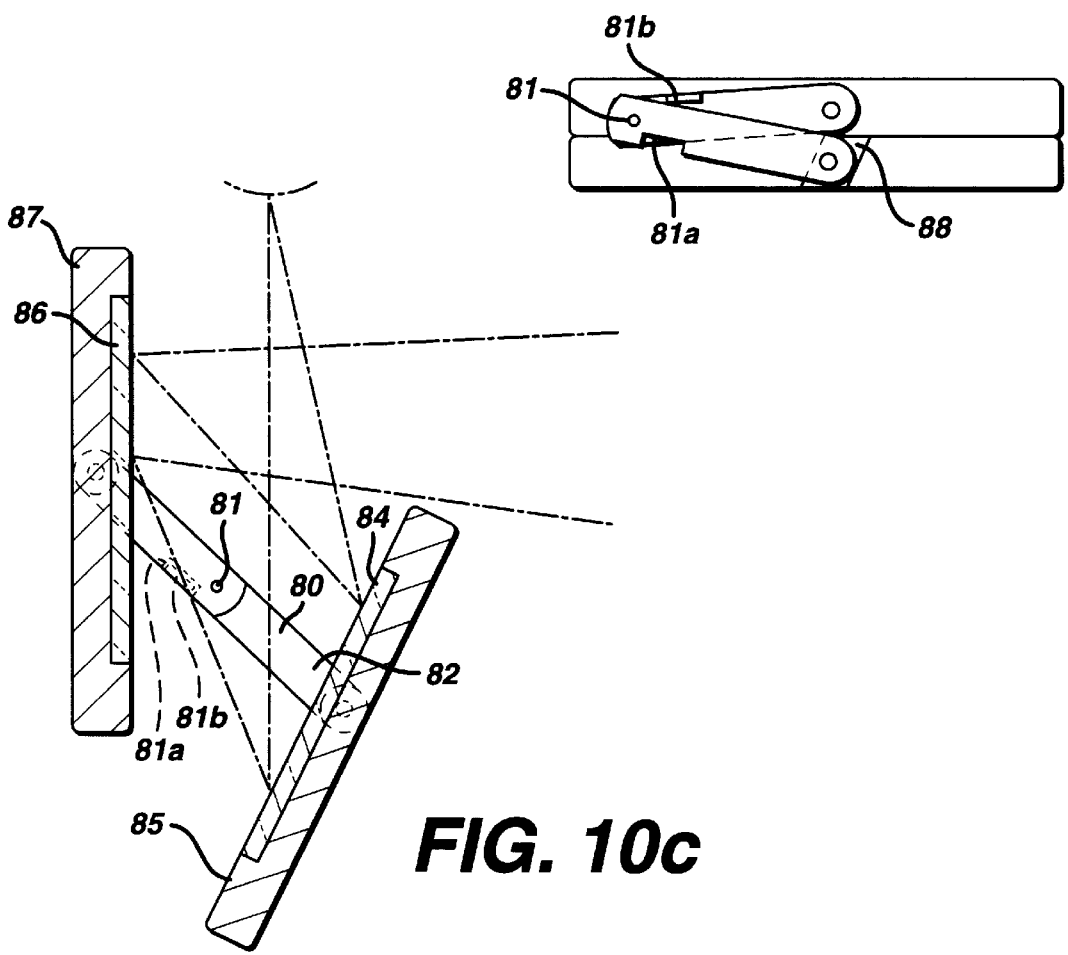

FORWARD DUAL VIEWING DEVICE

BACKGROUND OF THE INVENTION

Surgical procedures for the repair of a torn or detached retina are known. Such procedures include laser surgery, cryotherapy, scleral buckling, pneumatic retinopexy and vitreous surgery with air, gas, or silicone oil. In addition, gas has been used to repair macular holes. For eye surgery involving the use of a gas bubble, (i.e. retina detachment repair or macular hole repair) the patient must maintain a face down position for approximately four weeks post-operatively.

Many devices have been proposed to assist the patient during this four week period. One such device, sold by Palex Inventions, Inc., is shown in FIGS. 1 and 2. FIG. 1 shows a side view of the device. In dotted lines in FIG. 1 is the head up position of the head attachment portion of the device; specifically, the adjustable head strap, 1A, and the foam covered support, 6A. The head strap, 1 or 1A, is shown extended, as if fastened about the back of the head while the forehead rests against foam covered support, 6 or 6A. The adjustable jaw slide, at 2, adjusts the device into a head up or head down position. To put on the device, the head attachment portion is placed in the head up position, the foam covered bars, 7, disposed across the shoulders, and thereafter, the support belt, 3, fastened about the waist, and the head strap fastened about the back of the head while the forehead rests against support 6.

FIG. 2. is a front view of the device in the head down configuration, illustrating the foam covered support bar, 8, extending across the back of the apparatus, and adjustable height extensions 4. The device is made of aluminum tubing and foam padding, with a nylon support belt 3. An optional mirror, 5 in FIG. 1, may be mounted on an arm extending below the face of the wearer, and is said to provide safety while walking. While the Palex device claims to provide support to the head, neck, and back of the wearer, it is a cumbersome device, which provides no real viewing ability, leaving the wearer cut off from his or her surroundings. While the one mirror, 5, may provide an upside down view of objects in front of the wearer, it creates, at best, a crude, and potentially disorienting, navigational device.

A simple head support device, without a forward viewer, is described in an of advertisement by Oakworks in *Ophthalmic Surgery and Lasers,* July 1996. It comprises a horizontal, foam covered, inverted U-shaped head support, receiving the sides and top of the head, for comfortably maintaining the patient in a head down position. The support is mounted on a pole which rises from the front of the seat of what appears to be an ergonomic chair. U.S. Pat. No. 5,177,823 describes a similar Oakworks device in combination with a patient examining chair, or more complex chair construction. While these devices provide support for the head while the patient is seated in the device, they lack a portable forward viewer, limiting the activities of, and discouraging mobility in, the post-operative patient.

A headrest apparatus, with viewer, for use by patients convalescing from surgery to reattach a detached retina is shown in U.S. Pat. No. 5,408,713 to Stratton, et. al. The Stratton et al. headrest provides a table or a double mirror forward viewer, on a vertical support column. While the apparatus may be pulled up to a table, it leaves the patient at a distance from the table. The table top device of the present invention may be placed on top of the table in front of the patient It makes it easy for the patient to come directly up an existing table, such as their own dining or work table. When used on a table top, the device provides a comfortable headrest. Using the device of Stratton, the patient must constantly maneuver his feet about its forty centimeter base. In addition, the height of the Stratton apparatus limits its portability, realistically eliminates its ambulatory use, and renders it difficult to transport about the home, much less outside, to a restaurant or the home of friends or relatives. The table top device of the present invention yields many advantages over the floor based device of Stratton.

Numerous viewing devices have been provided to permit the supine viewer to view an object near his feet, e.g. a television, or medical service provider; see U.S. Pat. Nos. 3,019,689, 4,650,299, and 5,061,055. In addition, "glasses-type" devices with prisms rather than lenses, for viewing toward the feet, have been commercially available for a number of years. Another prism device, a camera lucida, used for drawing and copying, patented in 1807 by William Hyde Wollaston, utilizes a carefully placed prism to recreate the forward image on a drawing surface. Prisms in higher powers needed for forward viewing generally distort, making them inappropriate for use in general viewing devices, which are used for a moving or rotational view and for viewing objects at various distances. In fact, attempts to use prisms to "look around" produces a slightly delayed, but definite, nausea in the user.

There are a number of horizontal viewers for the bicyclists who ride in a face down position. Some are double mirror viewers. U.S. Pat. No. 4,375,316 to La Vantine describes a double mirror device which is rotatably attached to the crossbar of the handlebar. The viewing angles are shown in FIG. 1. FIG. 7 illustrates the adjustment of the bottom (eyepiece) mirror, followed by the adjustment of the top (objective) mirror by pulling back on its top edge and rotating the entire device about the crossbar. U.S. Pat. No. 5,148,327 to Gaxiola, referring specifically to La Vantine, describes what is believed to be better viewer, mounted at the centerline of the bicycle, forward of the handlebars, by attaching it to the center support post or goose neck of the bicycle. U.S. Pat. No. 5,305,153 to Kochocki utilizes spherical, bowl and ball mirrors to create viewing devices with curved reflecting surfaces to broaden the field of view. In addition, the device shown in FIGS. 4–7 uses multiple reflecting and viewing surfaces to produce greater height, as well as breadth, of view.

An alternative viewing apparatus worn on the face of the bicyclist (i.e. glasses or goggles) is shown in U.S. Pat. No. 4,679,916 to Roller et. al. Roller et. al. identifies the disadvantages of the two mirror bicycle mounted devices, as follows: 1) vibrations in the bicycle frame produce distortions in the image, 2) there is no side view, only a view directly ahead, which doesn't accommodate turning, and 3) it is too awkward and time consuming to constantly realign the mirrors while the rider alternates between sitting on the seat or standing on the pedals.

Another goggle or glasses type viewer is shown in U.S. Pat. No. 5,422,759 to Lee. The Lee apparatus is intended to be worn with the head erect. This device uses two mirrors or reflecting surfaces to produce a horizontally split image with the view downward presented in a mirror below the horizontal line of sight of the wearer. A similar device, shown in U.S. Pat. No. 5,173,720 to Lee et. al., allows the wearer to read a book in his lap without having to bend his neck. In contrast, the viewing devices of the present invention permit the user to view forward while encouraging a head down position.

Another viewing device is seen in U.S. Pat. No. 4,759,621 to Hawkins. This device permits the viewer to see the information shown on a computer screen, in a mirror at the level of a desk. The device is said to be useful for those who use bifocals, to eliminate the need to look up to a computer screen, and down to the desk. In fact, the device would be difficult for such a user, as the focal distance of the reflected view of the computer screen would not be the distance to the desktop, but a distance equal to the optical path to the viewing mirror, up to the object mirror, and across to the computer screen. Thus, the focal distance for the mirror view would be greater than the distance to the desktop, or the distance to the computer screen.

SUMMARY OF THE INVENTION

Applicants have invented viewing devices that permit the user to view forward, up, and down from a face down position. The viewing devices have few moving parts and are easy for the post-operative patient to use. Perhaps most importantly, use of the device involves a minimum of physical restriction for the patient, as by its optical design alone the device encourages the patient to maintain the necessary face down position. In one embodiment, the table top viewer, the device is sturdy enough to provide a much needed headrest while viewing forward, and light enough to be carried and used as a portable viewing device. In another embodiment, the pocket viewer, the device is so completely portable as to be carried in a purse or pocket. The viewing devices use two reflecting surfaces, or mirrors, an eyepiece mirror and an objective mirror. In the table top viewer of the present invention, the eyepiece mirror may be viewed from behind or above, and reflects the forward view up to the patient. Viewing forward using the device always involves bending over and down to obtain the view, thereby ensuring the patient will be encouraged to stay in a face down position.

In one preferred embodiment, the table top viewer, the device comprises a base, two parallel sides, each perpendicular to the base, and a top, forming an open-ended box type structure. When the device is placed on a table, the top serves as a headrest, and may be provided with a cushion or pad for further comfort. The eyepiece mirror is attached to the base and an objective mirror attached to a frame having an adjustable pivot. While resting their head on the headrest the patient may, with few adjustments of the pivot, view through the back of the device, the forward image, presented in the eyepiece mirror. Forward of the headrest, a head placement surface may be provided in the top of the device for correctly aligning the eyes of the patient in the back of the top of the device, but within a distance to obtain the largest possible view through the back of the device.

This embodiment of the viewing device invention may also be worn on a strap about the neck, hand held, or placed in the lap of the patient, or between patient's legs when seated so that the device is resting on the seat. When used in this fashion, i.e. by tilting it and looking through the front the patient must move his/her head forward and down in order to view over the objective mirror, into the eyepiece mirror. The table top viewer with a headrest maybe used in this manner whenever the patient chooses to be ambulatory, to sit away from a table, or when a tabletop is at an inconvenient height.

Also provided by the present invention are small, portable, or pocket devices which enable the user to view forward while looking down. As with all the embodiments of the invention, these pocket devices not only provide a front view, but encourage the user into a face down position. In one pocket version, the back edges of the mirror panels are joined along a pivot hinge. The view, from over and down into the eye piece mirror is the largest view possible from any particular size mirror, giving the pocket viewing device a generous view with the smallest possible mirrors. Another pocket device provides greater adjustability of the mirrors by providing a center panel between the mirrors, each mirror panel having a fully adjustable, pressure maintained hinge with the center panel.

The pocket viewers of the present invention may also be made with a pair of matching, parallel side hinges. In one such device, side hinges are attached near the front of the eyepiece mirror frame and at the lower sides of the objective mirror, and may be made to spring open, placing the hinges at an acute angle to the eyepiece mirror, and disposing the objective mirror above the eyepiece mirror. The objective mirror is fully adjustable with respect to the hinges.

In another embodiment of the pocket viewer the mirrors are attached at their sides by two jointed hinges. As the mirrors are separated, the hinges unfold, and when fully extended, may lock into a straight configuration. The eyepiece mirror has grooves, or other means for catching the hinge before it becomes perpendicular to the mirror, positioning the objective mirror slightly forward of the eyepiece mirror. The objective mirror is fully adjustable with respect to the other end of the hinges.

BRIEF DESCRIPTION OF THE DRAWINGS

FIG. 10a is a perspective view of an open, jointed hinged, pocket device of the present invention, FIG. 10b is a side elevation of the jointed hinged pocket device of FIG. 10a in its closed position, and FIG. 10c is a cross-sectional view of the jointed hinged pocket device of FIGS. 10a and 10b.

DETAILED DESCRIPTION OF THE PREFERRED EMBODIMENTS OF THE PRESENT INVENTION

Figure 1:
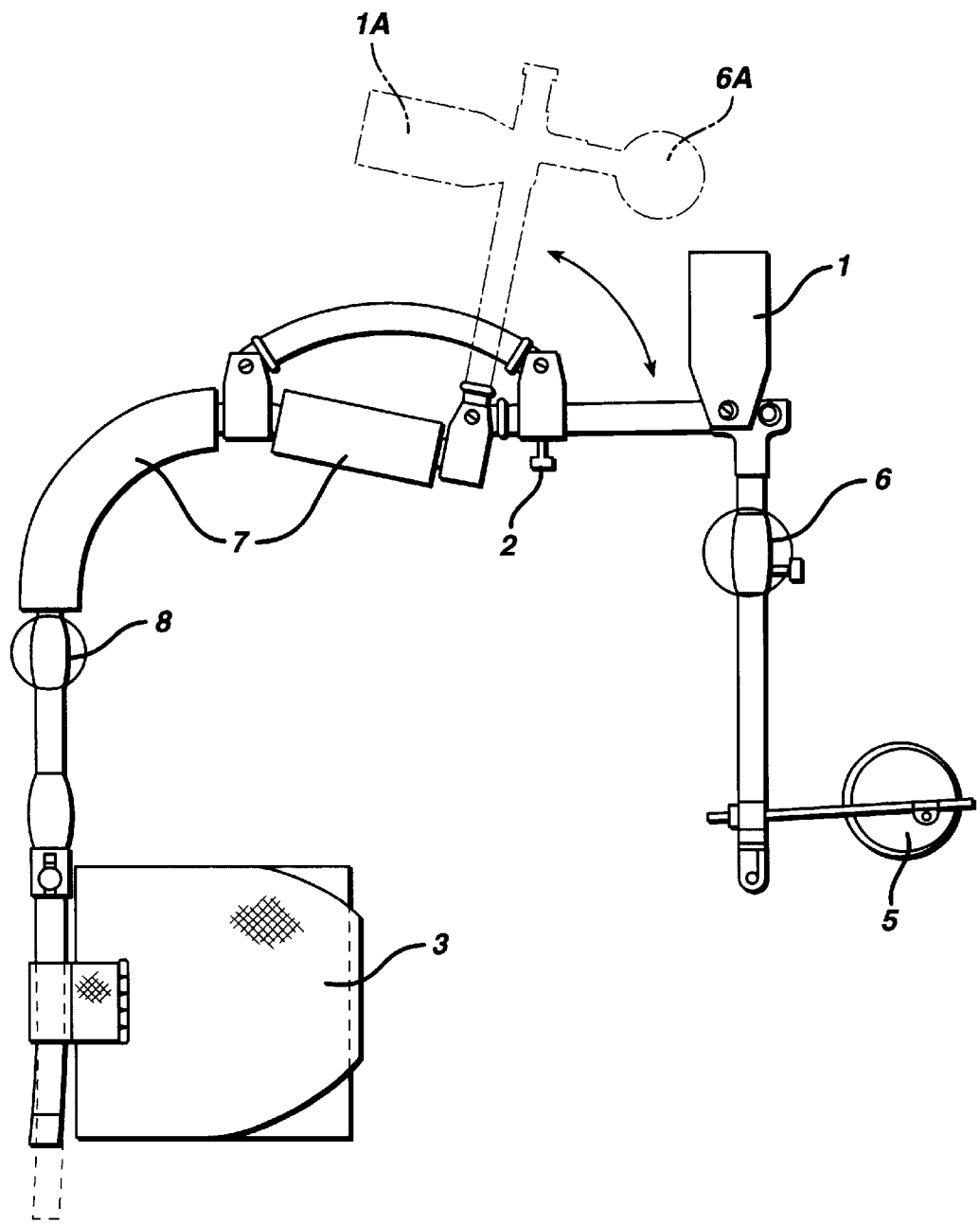
FIG. 1. is a side view of a prior art device sold by Palex Inc.
Figure 2:
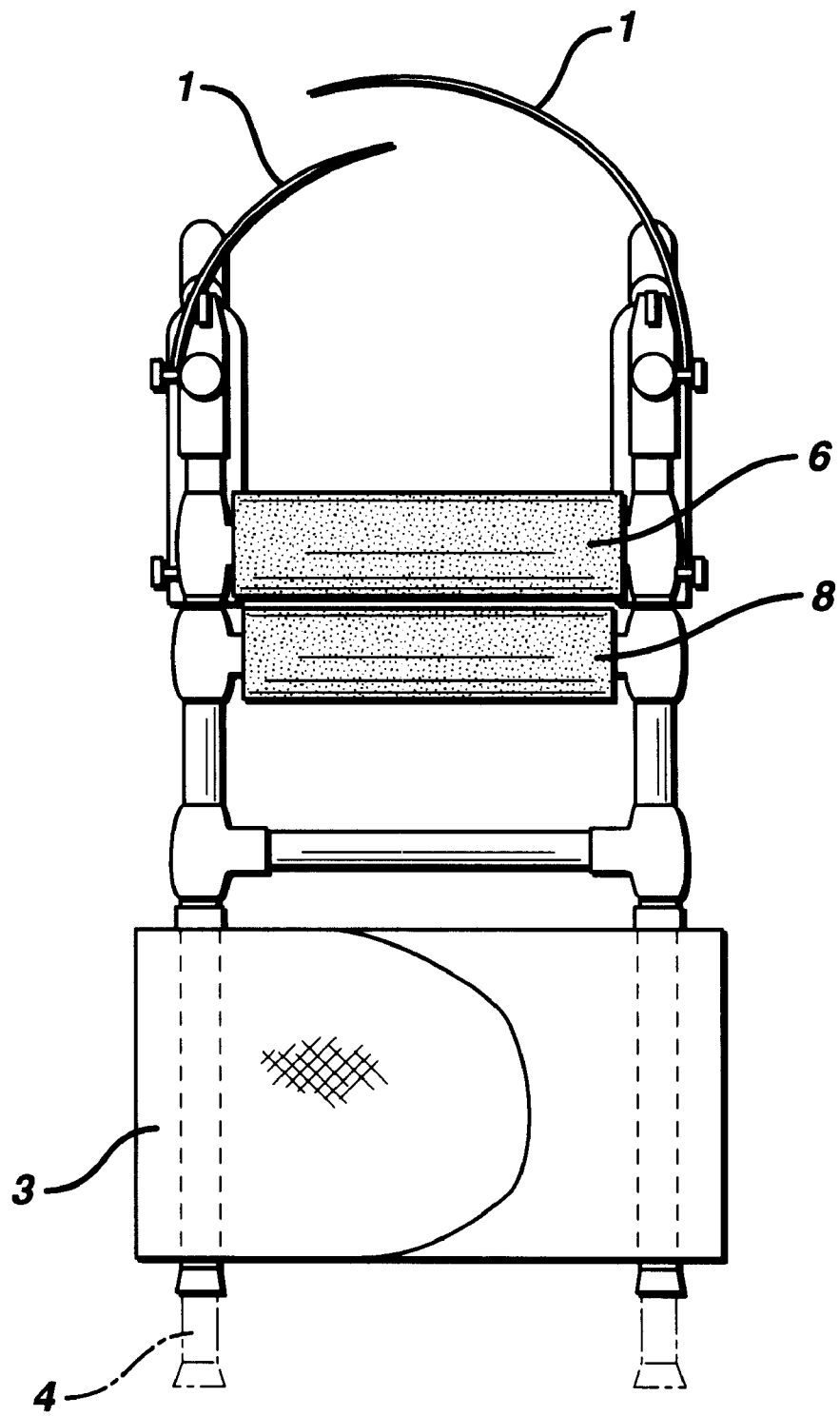
FIG. 2. is a front view of the Palex device of FIG. 1.
Figure 3:
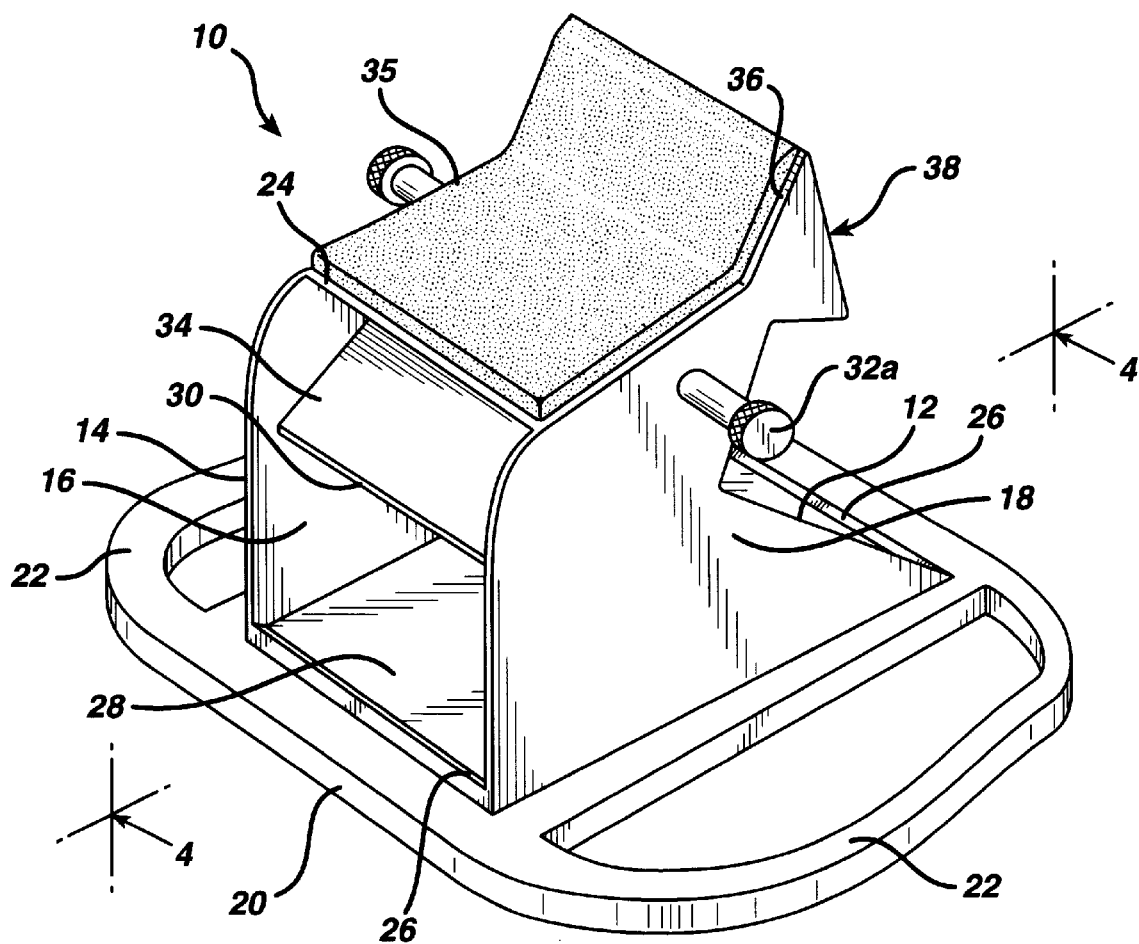
FIG. 3 is a perspective view of one embodiment of the table top viewing device, of the present invention.
Figure 4:
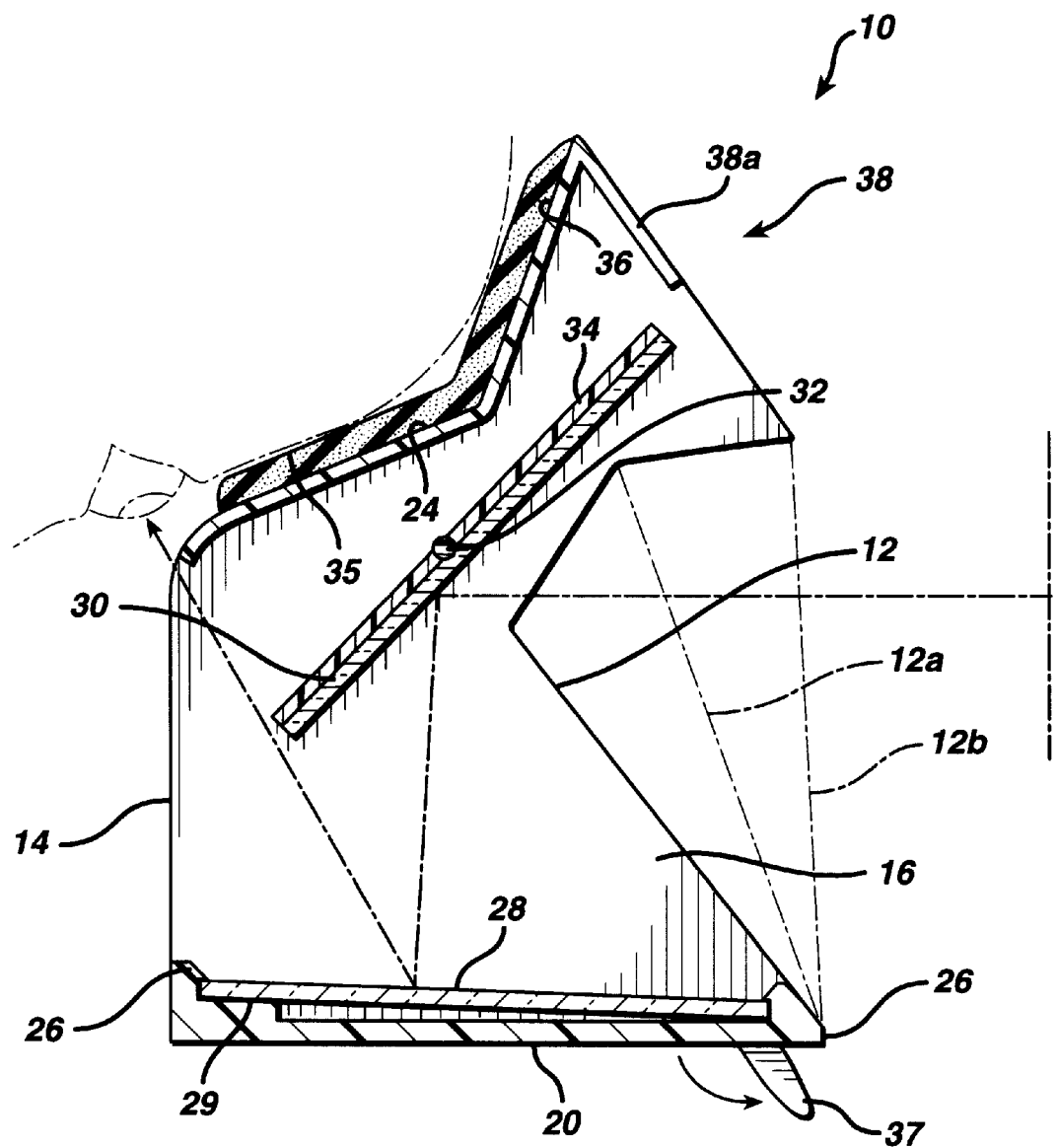
FIG. 4 is a cross-sectional view of the device of FIG. 3, taken along lines 4—4 of FIG. 3.

Referring to FIGS. 3 and 4, the table top viewing device, shown generally at 10, has a base 20, with two side edges, and sides 16 and 18 The sides are attached substantially perpendicularly to the base and parallel to each other, along the sides of the base. The sides 16 and 18 have front and back perspectives, 12 and 14, which also indicate the front and back of the base and device. The base, 20, may be extended past the sides to form one or more handles, 22, generally planar to the base, allowing the user to carry the device at their side, with the flat base next to their body. The device has a top, 24, attached to and generally perpendicular to the sides. The sides, base and top form an open-ended box type structure; open to the front and the back. It is preferred that the top not be parallel to the base, but have a gentle slope upwards from the back toward the front of the device.

A mirror, 28, or other reflecting surface, is mounted on the base. It may be mounted parallel to, or at a slight angle to, the base, preferably at an angle that opens to the back, as shown. The angle may be maintained in any number of known ways, such as with a shoulder or flange, 29, a simple incline, etc. The mirror may be secured within the device in any number of ways, as is well known in mirrored devices in general. In FIGS. 3 and 4, the mirror, 28, is secured by snapping it into resilient mounting means, 26. Though front and back mounting means are shown, a single mounting means may be sufficient. This mirror, 28, is termed the eyepiece mirror, as it is the mirror into which the viewer looks to see the reflected image.

Another mirror, 30, is also contained in the open ended box. This mirror, called the objective mirror, is mounted on a frame, 34. The frame is attached to a pivot, 32, extending from side to side, within the box. With little adjustment of the pivot, mirror 30 reflects the image of the object to be viewed, into the eyepiece mirror. As seen in FIG. 4, the objective mirror may be attached to a frame, 34, which has a pivot, or the mirror may be formed directly with or on the frame, and the objective mirror and the frame operate as one. In the embodiment shown in FIGS. 3 and 4 the pivot extends through the sides of the device to form the frame pivot adjustment means, here shown as a knob. In alternate embodiments the pivot adjustment means may extend through the sides into the box, to join the mirror, or mirror frame. It is highly preferred that the pivot adjustment means be located externally of the box, and include known means for adjusting, or rotating, and maintaining the chosen angle of the objective mirror. The pivot adjustment means are advantageously provided at both sides of the viewing device. While parallel sides permit the use of the largest objective mirror, the sides need not be precisely parallel, so long as the objective mirror has sufficient rotation.

Though the eyepiece mirror may be provided with means to adjust its position with respect to the base, it is preferred that the eyepiece surface be fixed, as adjustment of two mirrors makes viewing alignment difficult. In addition, adjustment of the eye piece mirror presents a greater potential for disorientation to the patient than adjustment of the objective mirror. The eyepiece mirror can be of less width than the objective mirror or either mirror can also be tapered if the extraneous images are bothersome to the viewer.

In the preferred embodiment, 10, of the viewing device of the present invention, the dimensions are intended to produce the most comfortable headrest height, upon the most common table height, approximately 76 centimeters. At this table height, the height of the top of the device, from base to top, is about 14–16 centimeters. As shown in FIG. 3 and 4, a headrest pad, 35, approximately one centimeter thick is provided, and included in the height of the top of the device. In FIGS. 3 and 4, the height of the top rises at about a 25 degree angle, from 13 cm. at the back edge, to 15 cm.

In the preferred embodiment of the headrest viewing device, shown in FIG. 3 and 4, the objective mirror frame pivot is located so close to the top of the device that an incline in the top, 24, is required to accommodate the rotation of the front of the objective mirror. This is done to provide the maximum distance between the mirrors, to produce the largest back view from any given size mirror. As best shown in FIG. 4, a steep incline portion of the top, e.g. a 50 degree rise from the headrest portion of the top surface, has been used to create a head positioning surface, 36. As illustrated in FIG. 4, use of a head positioning surface automatically places the eyes of the patient at the best distance behind the top of the device to take advantage of the greatest area of the eyepiece mirror. As also best seen in FIG. 4, the device is preferably provided with a front closure surface, attached to the sides and top, and shown generally at 3 8, to contain the mirror edges, enhancing the safety of the patient. Because of the steep incline in FIGS. 3 and 4, the front closure surface angles down steeply towards the front of the device. It is contemplated that the closure surface might be less steeply angled, level, or even rise slightly to the front of the device, especially if many other uses than tabletop use are contemplated. To accommodate viewing close objects situated above the device, or when the table top viewer is placed on the seat between the user's legs, the device is provided with tilting means for elevating the front of the device. In the embodiment shown in FIG. 4, the tilting means comprises at least one leg, 37, attached to the base, preferably hinged to the base so, and each leg provided with a mating recesses in the base, so the leg can be swung out from the recess to an angle of at least about 180 degrees when it is desired to tilt the device, and stored in its recess when it is not in use.

In constructing the table top embodiments of the present invention, many different materials may be used. The sides, base and top may be constructed of e.g. wood, plastic, cardboard, reinforced fiberboard, or other material strong enough that in a box type structure will support the head. It is not necessary that the base be a solid piece, a lightweight but strong framework being sufficient. It is preferred that the sides and top be solid enough to cut out extraneous visual images. Shown in FIG. 4, are front perspectives, 12, 12*a*, and 12*b*, which provide progressively more closure to the box, but add a bit of the reflection of the inside surface of the device, to the image in the eye piece mirror. The reflecting surfaces can be made of silvered glass, polished metal, Mylar, anodized aluminum coated plastic, or other image reflecting material. Back surface reflecting glass mirrors are shown in FIGS. 3–6, but front surface reflecting materials may easily be used, as is known to one in the art.

Figure 5:
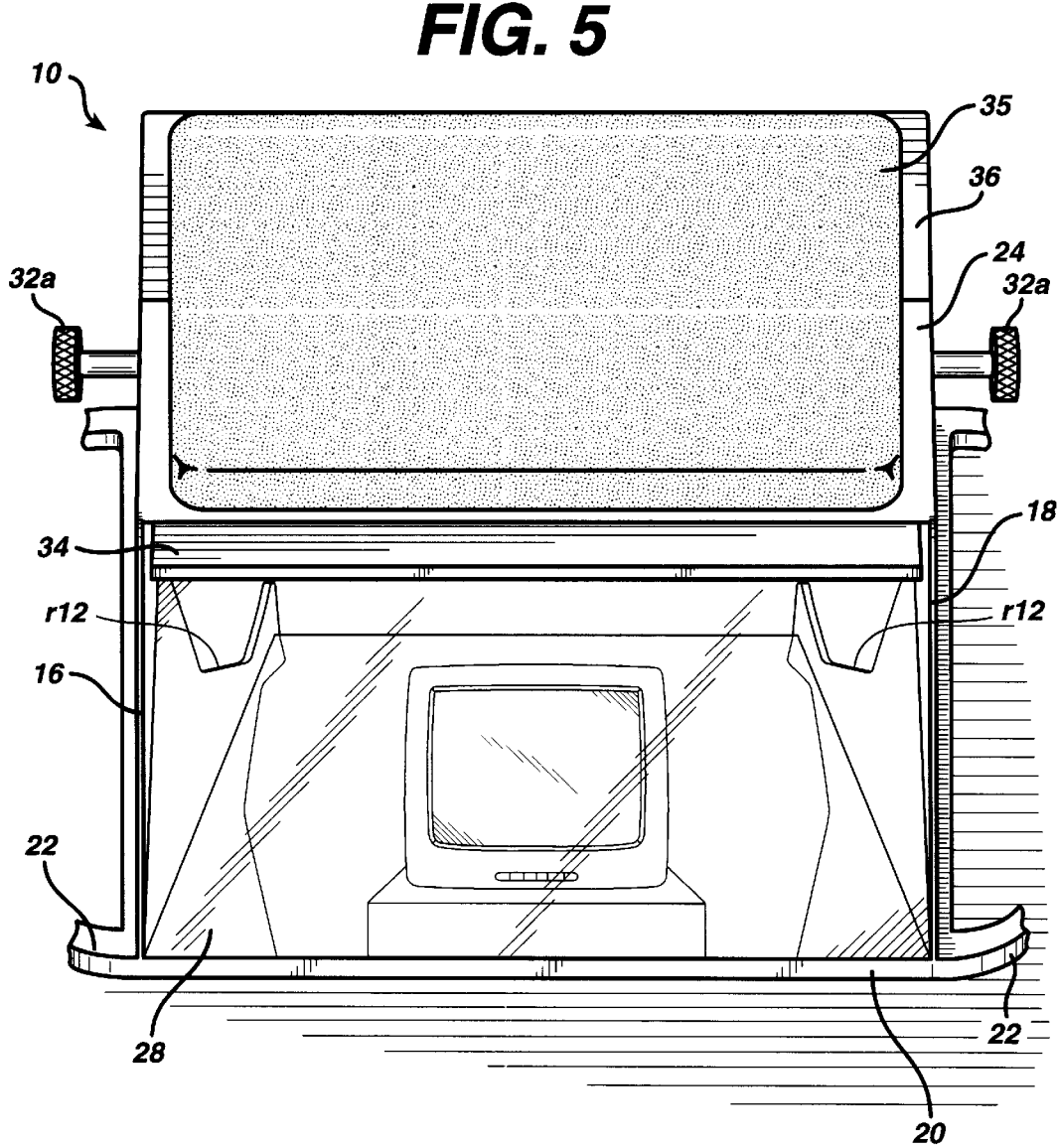
FIG. 5 is a view through the back of a table top viewing device of the present invention, showing the view in the eyepiece mirror, and illustrating the reflection of the front prospective or cut-out, 12.

FIG. 5 illustrates the view provided in the eyepiece mirror, viewed through the back of table top device similar to the embodiment shown in FIGS. 3 and 4. The view forward of the device is seen reflected in the eyepiece mirror, 28, in this instance a T.V. The reflections, r12, of the front perspective, 12, are also shown Adjustment of the objective mirror would provide a view of whatever is above the T.V., and perhaps a little of what might be below the T.V. in the view forward of the viewing device.

Figure 6:
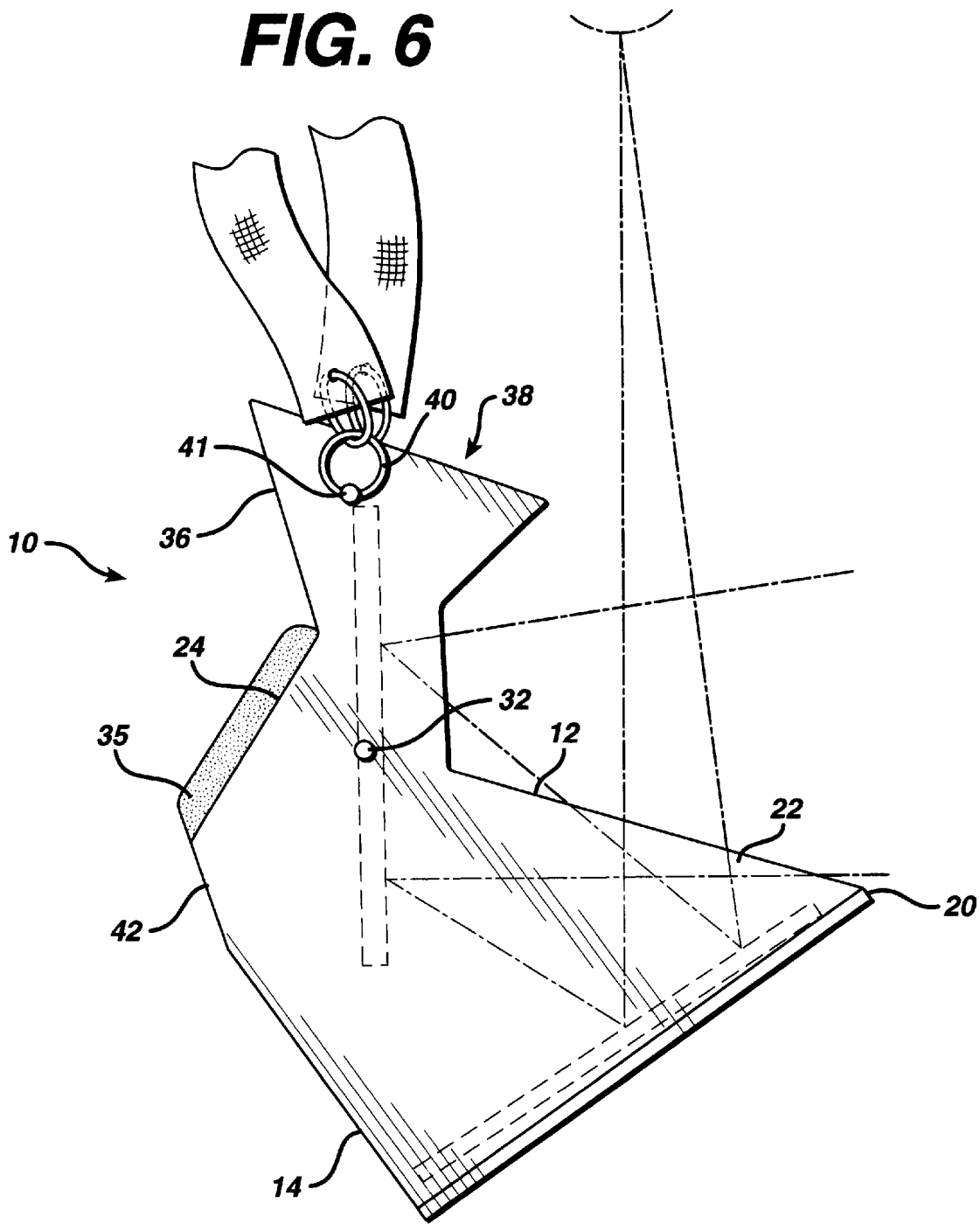
FIG. 6 is a side view of a viewing device similar to the device of FIG. 3, as adapted for use with a neck strap.

FIG. 6 illustrates another embodiment of the table top viewing device, similar to the devices of FIGS. 3–5, including refinements in the device. When seated away from a table, when moving about, when a headrest is not required, or when the user wants their hands free, the device is most advantageously viewed through the front. To accommodate this use, the device may be provided with one or more strap attachment means for attachment to e.g. a camera strap. Use of the device with a strap about the neck of the user, positions the device at an angle, as illustrated in FIG. 6. The strap attachment means 40, is a loop pivotally attached to the side of the device by mounting means such as an eyed-screw through which the loop can been disposed. Adjustment of the strap length will easily accommodate different users and different activities. To balance the device properly, it is preferred that the attachment means be located above the frame pivot, near the front of the device. When used in this position, the patient is more mobile, and enjoys the larger view obtained from the "over the objective mirror" approach to the eye piece. It should also be noted, that this use of the device requires the patient to bend their head out and down, achieving the face down position. Loss of the head down position will be immediately communicated to the user by the necessity to re-adjust the object mirror, and the subsequent loss in height of the view available.

In another preferred embodiment, the back edge of the top and sides may be cut away at the back, providing a balancing surface, 42, at 45–60 degrees to the base, as shown in FIG. 6. When worn with a strap, the viewing device may be used when the patient wants their hands free, and wants no table or impediment while engaging in an activity such as working in front of a computer, playing cards, or holding a stair railing. It should be noted that any of the table top device of the present invention may be hand held, or simply placed in the patient's lap. Each of these uses takes a minor adjustment of the reflecting surfaces, but requires that the patient maintain a head down position.

The pocket portable viewing devices of the invention permit greater ambulation, and, as the name indicates, can be easily brought along and stored in a pocket to be used whenever desired. Though smaller mirrors permit the manufacture of smaller, more easily stored devices, the smaller mirrored devices yield a smaller picture or view. It is preferred that the mirrors and frames of the pocket devices have a width greater than their depth, and in all the pocket devices the letters f and b shall denote the front and back edges of the mirror frames; the side edges of the frames being the edges which lie between the front and back edges. In the pocket devices of the present invention, the term base is often used interchangeably with eyepiece mirror frame. In each of the pocket devices, the mirrors and frames are connected by hinges such that when opened, the mirrors reflect an image or object sequentially, from one to the other. It is preferred that the hinge arrangements bring the mirrors into alignment in the closed position, to make the closed device as small as practicable.

It is also preferred that the pocket devices have closure means, and sometimes, restraining closure means, to maintain their small compact shape. The closure means may comprise hinge locks or locking means on the side of front edges of the mirror frames. The pocket devices, can be advantageously manufactured from many light weight materials such as plastic, coated foam, and Mylar.

Figure 7A:
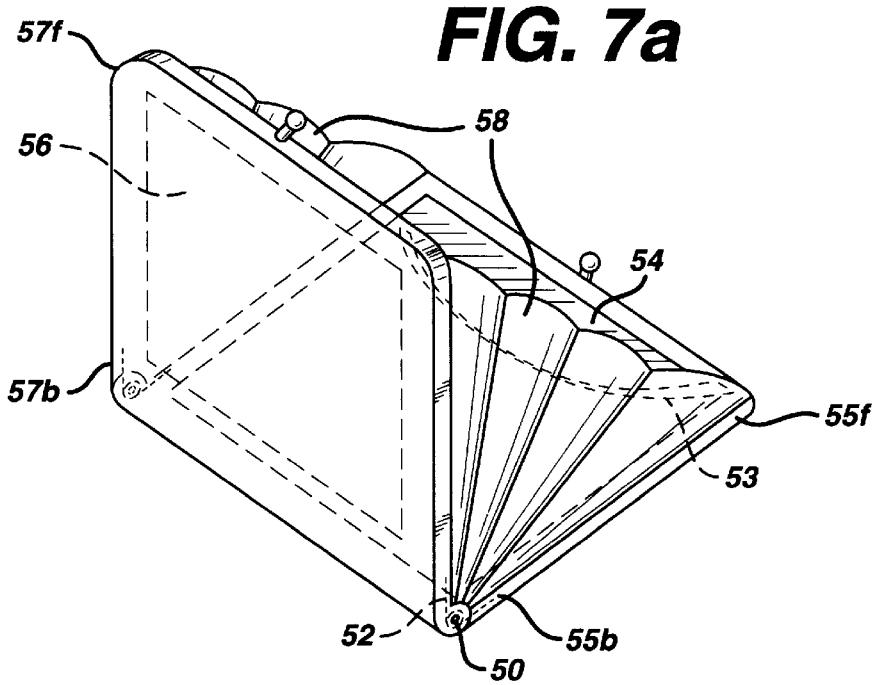
FIG. 7a is a perspective view of an open clamshell like pocket device of the present invention.
Figure 7B:
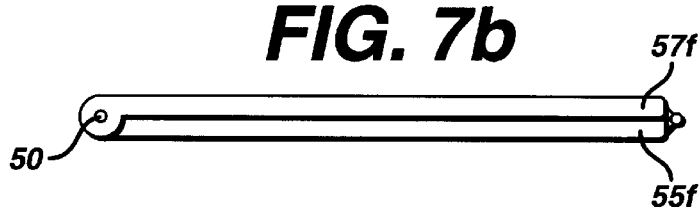
FIG. 7b is a side elevation of the clamshell like pocket device of FIG. 7a in its closed position.
Figure 7C:
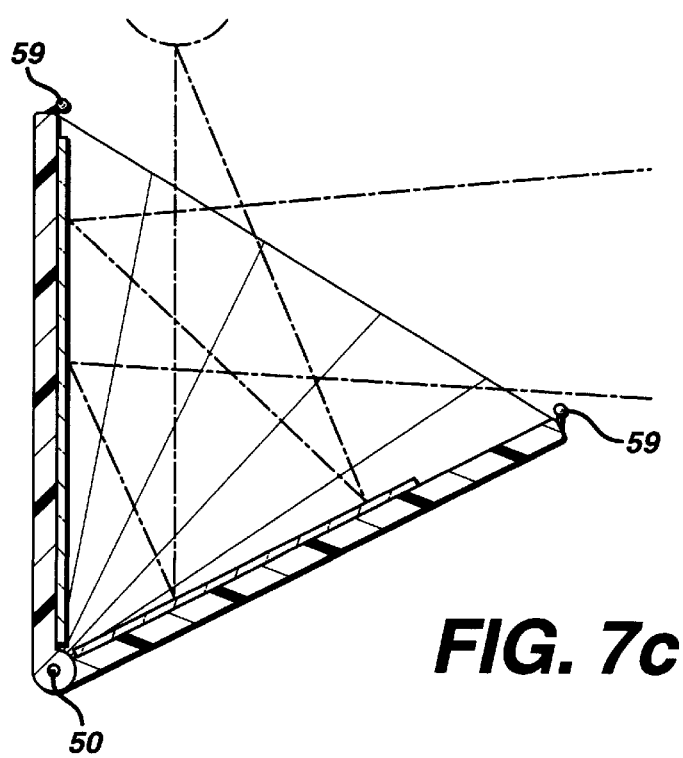
FIG. 7c is a cross-sectional view of the clamshell pocket device of FIGS. 7a and 7b.

In one embodiment of the pocket device of the present invention, illustrated in FIGS. 7a–c, the eyepiece and objective mirrors, 54 and 56, respectively, are mounted on or in frames 55 and 57, respectively. The back edges of the frames are joined along a common pivot hinge, 50, such that the mirrors face each other. The hinge may be provided with a spring, 52, to pop open the mirrors to a 60 degree angle, and permit manual tilting of the whole device to view objects. Alternatively, the device may be provided with a brace, 53, which when the device is closed lays flat between the mirrors and/or frames Preferably, the brace has one end thereof permanently attached to one of the mirror frames, with the other mirror frame provided with a slot for receiving the free end of the brace. The length of the brace, location of the brace mounting, and brace end receiving slot, being chosen to creating a 60 degree angle between the mirrors when braced open. In the embodiment shown in FIGS. 7a–c, the device is provided with side panels 58, which are collapsed in the closed configuration, as e.g. by accordion or other folds, and extend on opening the device, to fill the side openings between the mirrors or mirror frames.

In an alternative construction, the hinge may be a fully adjustable hinge, permitting the user to place the objective mirror at any angle to the eyepiece mirror, but with sufficient resistance to maintain the set angle until force is again applied to the frames to reset the angle. This type of hinge is in common usage in the cosmetic industry for hinged compact cases, and will be referred to generally as a compact-type hinge. The eyepiece mirror is about 60% of the depth of the objective mirror, and held at a constant 60 degrees from the objective mirror.

This pocket device has no mirrors to adjust, and changing the view, to the sides, and up ad down, involves only slight movement by the patient, producing almost no potential for disorientation, and keeping the patient constantly in a face down position. This pocket device may be provided with closure means to restrain the spring and maintain the device in its closed position. The closure means illustrated in FIGS. 7a–c is a two piece mating closure, formed of slightly offset beads at the front edge, as is commonly known in the art. Alternative closure means for restraining a spring opening device, such as a tab and mating indent in the front edges of the mirror frames, are well known in the art.

Figure 8A:
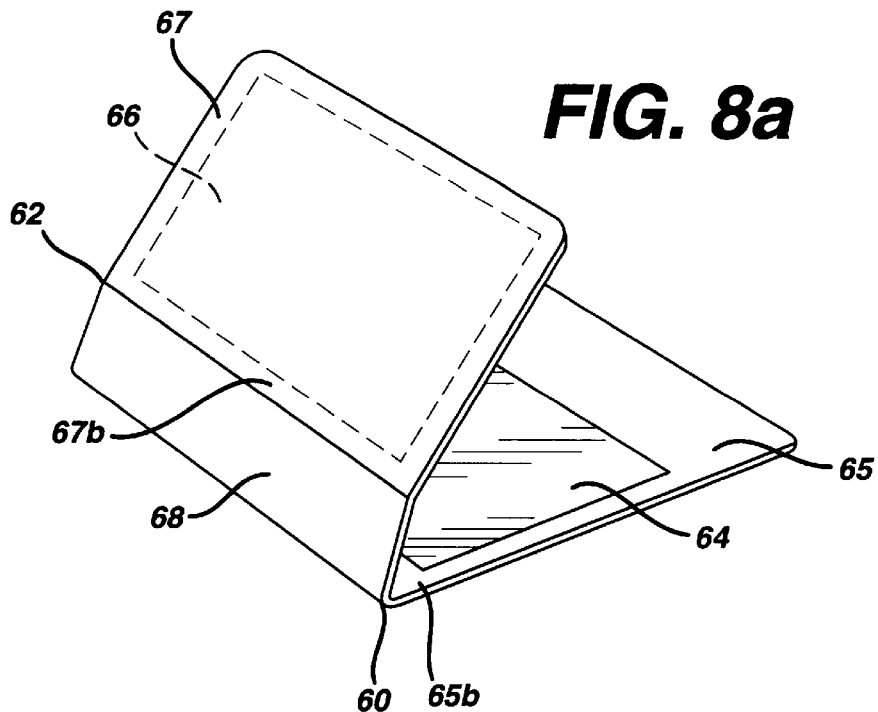
FIG. 8a is a perspective view of a three panel binder-type pocket device of the present invention.
Figure 8B:
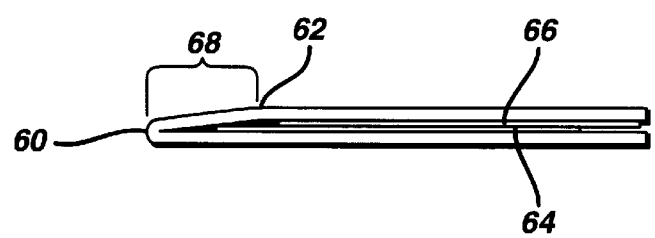
FIG. 8b is a side elevation of the three panel binder-type pocket device of FIG. 8a in its closed position.
Figure 8C:
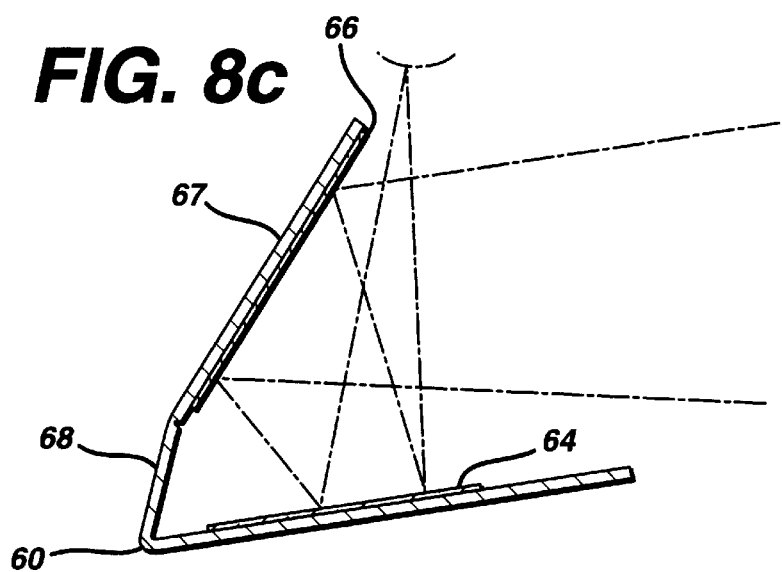
FIG. 8c is a cross-sectional view of the three panel pocket device of FIGS. 8a and 8b.

In another embodiment of the present invention, shown in FIGS. 8a–c, the eyepiece and objective mirrors, 64 and 66, respectively, are attached to mirror frames, 65 and 67 As seen in FIG. 8a, the device has a rectangular back panel, 68, with opposing length edges and side edges. Each of the mirror frames has a hinge connection along its back edge, to a length of panel 68. Frame 65 is connected at its back edge to back panel, 68, along pivot hinge, 60, and frame 67 is hinged at its back edge, to the back panel, 68, along pivot hinge, 62, producing a doubly adjustable connection between the mirrors. The pivot hinges 60 and 62 may be of the same or different construction. In a preferred embodiment, both hinges are of the compact-type hinge used for plastic cosmetic compacts; fully and freely adjustable, and able to maintain a particular angle until reset by the user.

The back panel is much wider than its height. One example of this viewing device, the three panel double hinged viewer, has a back panel about 1¼ inches by 5¼ inches, with mirror frames about 5¼ inches wide and about 4¼ inches deep. This, in general, is the preferred size of the mirrors and mirror frames of all the pocket devices. As seen in FIG. 8c, the eyepiece mirror may have a depth greater than about 60% of the depth of the objective mirror, due to the double hinge, and back panel height, which may be manipulated, as shown in FIG. 8c, to place the back edge of the objective mirror in front of the back edge of the eyepiece mirror.

Figure 9A:
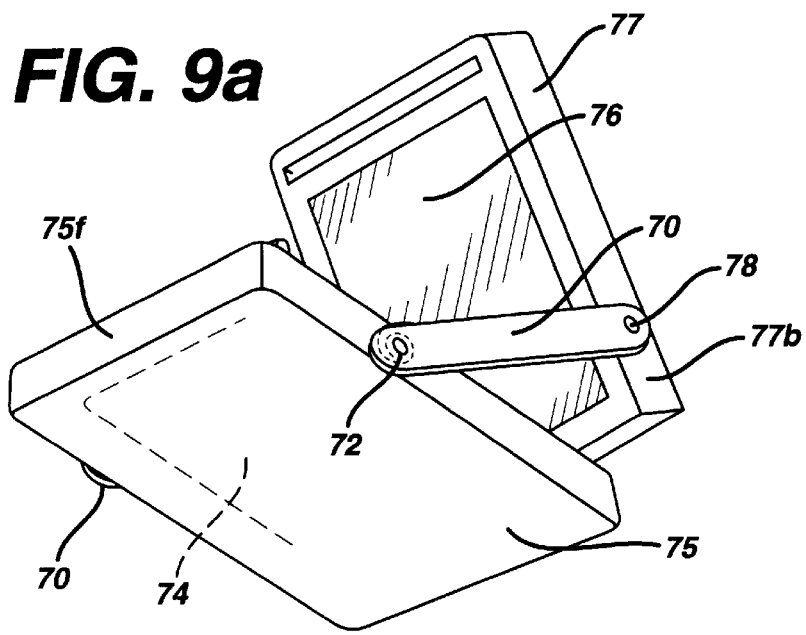
FIG. 9a is a perspective view of an open side hinged pocket device of the present invention.
Figure 9B:
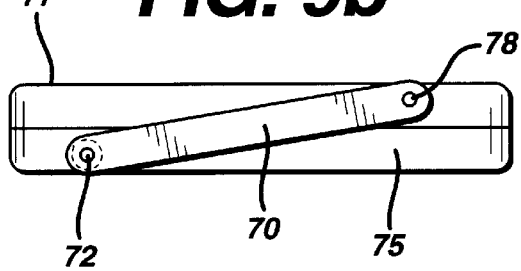
FIG. 9b is a side elevation of the side hinged pocket device of FIG. 9a in its closed position.
Figure 9C:
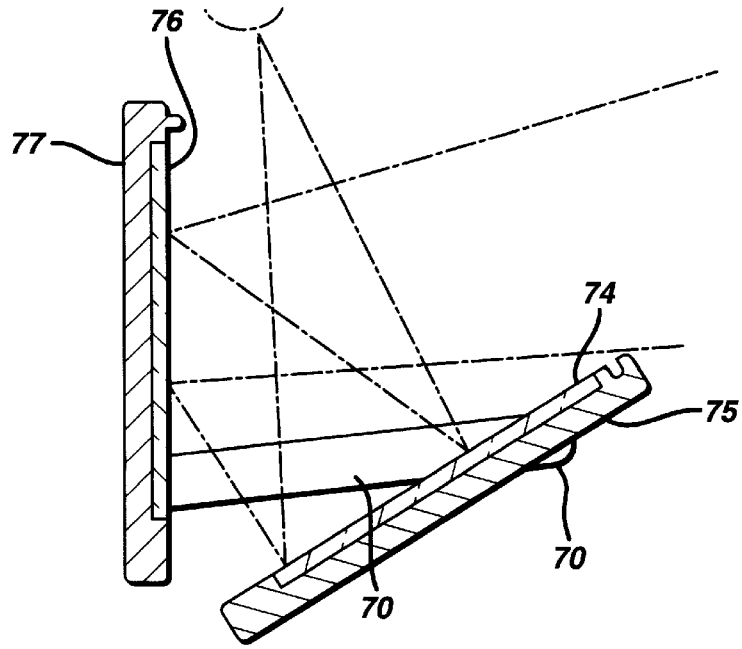
FIG. 9c is a cross-sectional view of the side hinged pocket device of FIGS. 9a and 9b.

FIGS. 9a–c illustrate another embodiment of the invention which uses two matching side hinges to attach the mirror frames. As seen in FIG. 9a, eyepiece and objective mirrors, 74 and 76, respectively, are mounted into frames 75 and 77, respectively. A single hinge, 70, is provided at each side of the mirror frames. The hinges, 70, are rotatably attached to the front of the side edges of the eyepiece mirror, and the back of the side edges of the objective mirror. In this manner, the device achieves the smallest size when closed, when, preferably the mirrors overlap. The bottom hinge connection, connecting the hinge to the eyepiece mirror, may be provided with a spring, 72, to pop up the hinge with respect to the eyepiece mirror, displacing the objective mirror away from the eyepiece mirror. The upper hinge connection, connecting the hinge to the objective mirror, provides a fully adjustable, pressure maintained pivot hinge connection between the hinge and the objective mirror. The hinge construction may comprise pivot means, 78, at the side of the frame, which may consist of a rod passing through the frame of the objective mirror, or mounts, such as posts, at the sides of the frame, about which the frame can be rotated. The rod or pivot mount is connected to the top of the hinge. In the pivot connection, be it between the rod and the frame, or the pivot mounts (or ends of the rod), the hinge connection is constructed of materials and dimensions to achieve an adjustable angle which is readily maintained until the user elects to readjust the angle. Hinge connections of this variety, e.g., hinges for cosmetic compact cases, are well known. When provided with a spring hinge, the device is preferably also provided with a restraining closure means, as described in relation to the embodiments of FIGS. 7 and 8, or the mating flange and groove shown in FIGS. 9*a* and 9*c*.

Figure 10D:
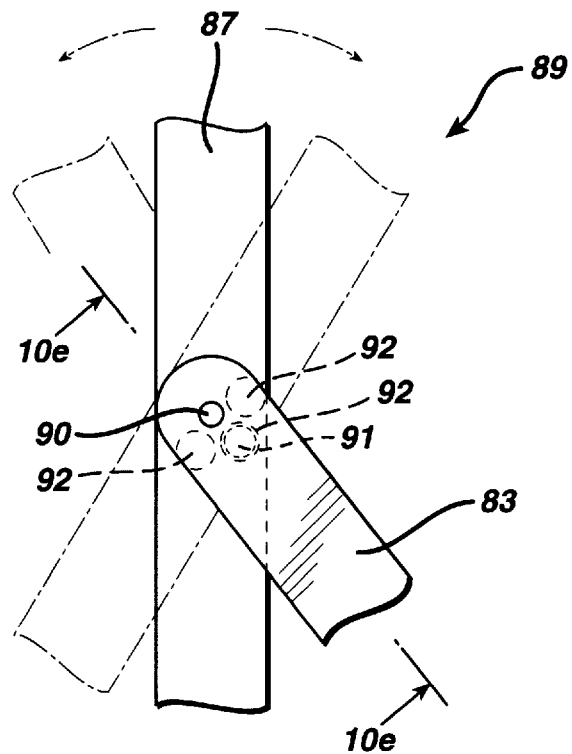
FIG. 10d is a side view of the hinge fastening of an upper leg of the jointed hinge to the side of the objective mirror.

One preferred embodiment of the pocket device of the present invention is shown in FIGS. 10*a–e*. This device uses jointed hinges, which have two legs rotatably joined at hinge pivot, 81. The legs can be rotated until they overlap, or rotated to an extended position, in which position the legs are preferably provided with a hinge pivot locking means to prevent rotation greater than 180 degrees. Hinges of this construction are well known and come in a variety of sizes, but are perhaps best known as a Stanley table leg hinge, commonly used to position the legs of a card table. Two identical hinges must be used, with the only exception that hinge pivot locking means may be provided for only one of the hinges, as desired. Therefore, only one hinge will be described, with a locking means. As shown in FIG. 10*a*, the jointed hinge 80, has a lower leg, 82, and an upper leg, 84, rotatably connected at hinge pivot, 81. The eyepiece and objective mirrors, 84 and 86, respectively, are secured to their respective frames, 85 and 87. The lower leg, 82, of the hinge is rotatably connected to the eyepiece mirror frame, 83, by conventional means; perhaps the simplest of which is shown in FIGS. 10*d* and *e*, where a nail, screw, 90, or other fastening device having a head larger than the hinge mounting hole, is placed through the hinge mounting hole and driven into the site, (here the midside of the frames), where the hinge connection is desired. Many other rotatable hinge fastening are known and could be used with the viewing devices of the present invention. The upper legs, 83, of both hinges are rotatably connected to the frame, 87, of the objective mirror through a frame pivot or pivot mounts, as described in relation to the embodiment of FIGS. 9*a–c* . As shown in FIGS. 10*a–c*, the hinges are attached to the sides of the frames at about the midpoint of the sides.

In one preferred embodiment, the sides of the eyepiece mirror frame, 85, are provided with preset hinge restraining means, 88, in the form of cut-outs or recesses or other known means such as a restraining wall or flange, which receive or restraining the lower legs at an acute angle to the frame, which disposes the back edge of the objective mirror frame, (and mirror) in front of the back edge of the eyepiece mirror frame (and mirror).

Figure 10E:
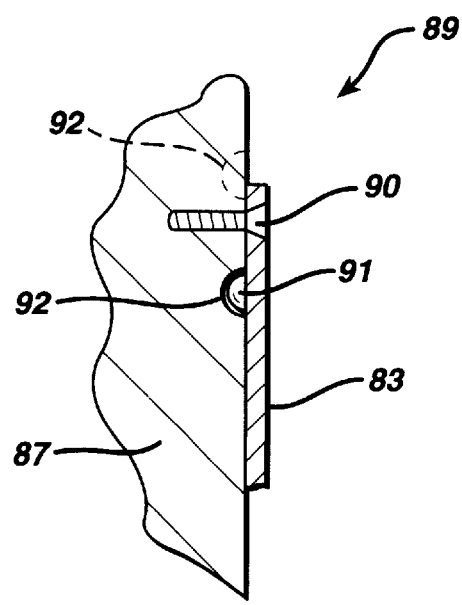
FIG. 10e is a cross-sectional view of the fastening of FIG. 10e, taken along lines 10e—10e.

The hinge connection between the eyepiece mirror frame and the upper legs of the hinge may be provided with means, 89, for restraining the frame at one or more preset positions. As shown in FIGS. 10*d* and 10*e*, means 89 may comprise curved spring mounts, such as a spring mounted ball, 91, on the inner surface of the hinge leg, and one or more recesses, 92, which receive the curved spring mounts, in this case the spring ball, of the hinge, and restrain the frame against further rotation until the user applies a small force to the frame, popping the ball out of the recess. A series of recesses may be provided corresponding to a number of preset positions or angles of the frame, 87, to the upper leg of the hinge. The series of recesses are advantageously provided along a curve, to permit the use of the smallest possible recesses, and to provide the closest mating of the ball and recess.

When fully extended, the hinge legs have a locking means, such as the matching cut-away and tab, 81*a* and 81*b*, to prevent further rotation of the legs beyond 180 degrees. The hinge pivot, 81, may also be provided with adjusting means to temporarily secure the angle between the hinge legs, such as a nut-and-bolt screw-down mechanism, or other means as are well known in the art.

In the pocket devices illustrated in FIGS. 9*a–c* and 10*a–e*, the hinges and their attachments may be located in a slots along the sides of the of the frames, leaving the outside of the device smooth. In addition, as the eyepiece mirror is preferably narrower than the objective mirror, the objective mirror frame may be provided with a rim or wall to enclosed the side edges and front edge of the eyepiece mirror, when the device is closed.

While a number of preferred embodiments have been described herein, and certain modifications illustrated and suggested, other variations and changes may be made without departing from the spirit of the invention.

We claim:

1. A viewing device comprising:
   a housing having a horizontal bottom surface, a top surface and two side surfaces connecting the top surface to the bottom surface; said top surface disposed at an angle to said bottom surface;
   a first mirror fixed to said bottom surface, and a second mirror pivotally connected between said side surfaces adjacent to said top surface;
   said top surface having a first and second portion; said first portion disposed at an angle relative to said second portion.

2. The viewing device according to claim 1 further comprising at least one handle; said at least one handle extending from one of said side surfaces adjacent to said bottom surface.

3. The viewing device according to claim 1 wherein said first mirror is fixed at an angle relative to said bottom surface.

4. The viewing device according to claim 1 wherein a strap is attached to said side surfaces.

5. The viewing device according to claim 1 wherein each of said side surfaces has a first edge and a second edge wherein the first edge is at an angle relative to the second edge.

* * * * *